United States Patent
Iyengar et al.

(10) Patent No.: US 9,221,769 B2
(45) Date of Patent: Dec. 29, 2015

(54) PROCESS FOR THE PREPARATION OF BIS-(1(2)H-TETRAZOL-5-YL)-AMINE MONOHYDRATE

(71) Applicants: Deevi Sarangapani Iyengar, Hyderabad (IN); Anil Saikia, Hyderabad (IN); Nagi Reddy Bhimireddy, Hyderabad (IN)

(72) Inventors: Deevi Sarangapani Iyengar, Hyderabad (IN); Anil Saikia, Hyderabad (IN); Nagi Reddy Bhimireddy, Hyderabad (IN)

(73) Assignees: TK HOLDINGS INC., Armada, MI (US); HY-GRO CHEMICALS PHARMTEK PRIVATE LIMITED, Secunderabad (IN)

( * ) Notice: Subject to any disclaimer, the term of this patent is extended or adjusted under 35 U.S.C. 154(b) by 0 days.

(21) Appl. No.: 13/846,385

(22) Filed: Mar. 18, 2013

(65) Prior Publication Data
US 2014/0066630 A1    Mar. 6, 2014

(30) Foreign Application Priority Data
Sep. 5, 2012 (IN) .......................... 3656/CHE/2012

(51) Int. Cl.
*C07D 257/06* (2006.01)

(52) U.S. Cl.
CPC .................................. *C07D 257/06* (2013.01)

(58) Field of Classification Search
None
See application file for complete search history.

(56) References Cited

U.S. PATENT DOCUMENTS

| 2003/0060634 A1 | 3/2003 | Naud et al. |
| 2008/0207914 A1 | 8/2008 | Toda et al. |
| 2010/0261912 A1 | 10/2010 | Toda et al. |

*Primary Examiner* — Alicia L Otton
(74) *Attorney, Agent, or Firm* — Oliff PLC

(57) ABSTRACT

A process for the preparation of Bis-(1(2)H-tetrazol-5-yl)-amine monohydrate.

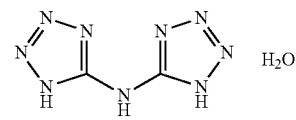

This preparation process is carried out by the reaction between sodium dicynamide and sodium azide in presence of a dilute solution of an inorganic acid solution in aqueous medium.

7 Claims, No Drawings

PROCESS FOR THE PREPARATION OF BIS-(1(2)H-TETRAZOL-5-YL)-AMINE MONOHYDRATE

FIELD OF THE INVENTION

The present invention relates to an improved process for the preparation of Bis-(1(2)H-tetrazol-5-yl)-amine monohydrate of the formula (I) by the reaction of sodium dicynamide and sodium azide, by adding a 6 molar solution of hydrochloric acid in the presence or absence of a catalytic amount of boric acid (1% to 5% by weight) into the reaction mixture for a period of 2-8 hour at 55° to 58°

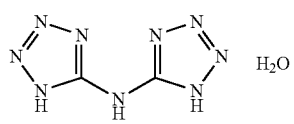

BACKGROUND OF THE INVENTION

Bis-(1(2)H-tetrazol-5-yl)-amine monohydrate of the formula also known as BTA having the structural formula (I), useful as a gas generant. According to the available literature, it is prepared by the reaction of sodium dicynamide with sodium azide in the presence of inorganic or organic acids.

In the patent U.S. 2003/0060634, described this reaction in the presence of hydrochloric acid (HCl), sulphuric acid (H2SO4), phosphoric acid (H3PO4), nitric acid (HNO3), perchloric acid (HClO4) and the mixtures thereof. Also some organic acids like trifluoro acetic acid, trifluoromethane sulfonic acid and methane sulfonic acid. But this patent preferred hydrochloric acid and the most preferred the addition of 1.6 molar hydrochloric acid solutions at refluxing temperature, over the course of 24 hours with 85.6% yield. But due to the formation of very fine amorphous product, it is difficult to filter the product during the scale up process.

In the patent U.S. 2008/0207914 mentioned the addition of concentrated hydrochloric acid at 60° C. for a period of 10-42 hour followed by reflux for another 24 hour yielded 86-92% with 99.4% purity by HPLC.

In the patent U.S. 2010/0261912 described the preparation of bis-(1(2)H-tetrazol-5-yl)-amine monohydrate by using boric acid, 63% sulphuric acid and 90% acetic acid. The addition was done for a period of 3 hour followed by maintenance of 10 to 42 hour.

SUMMARY OF THE INVENTION

In accordance with the present invention relates to an improved process for the preparation of the bis-(1(2)H-tetrazol-5-yl)-amine monohydrate. In this method sodium dicynamide reacted with sodium azide in presence of 6 molar hydrochloric acid and a catalytic amount of boric acid. The reaction carried without boric acid gave bis-(1(2)H-tetrazol-5-yl)-amine monohydrate in amorphous state with 90-93% yield, which gave a difficulty during filtration. But the use of 10% boric acid along with 6 molar hydrochloric acid gave 93-95% in yield with fine crystal instead of amorphous powder.

DETAILED DESCRIPTION OF THE INVENTION

The present invention is an improved process for the preparation of the bis-(1(2)H-tetrazol-5-yl)-amine monohydrate. Bis-(1(2)H-tetrazol-5-yl)-amine monohydrate was prepared as follows:

In this method sodium dicynamide and sodium azide was dissolved in water and then heated the mixture to 55° to 58° C. "At this temperature, the solution of boric acid (1% to 10%) and dilute hydrochloric acid was added for a period of 2 to 8 hour". After complete addition of hydrochloric acid, heated the reaction mixture to reflux for another 25 hour.

After 25 hour maintenance, cooled the reaction mixture to 55° C. and adjusted the pH of the reaction mass to <1 using the same molar concentration of hydrochloric acid.

Cooling to 25° to 30° C. followed by filtration and washing with water gave the bis-(1(2)H-tetrazol-5-yl)-amine monohydrate.

The crystalline product was isolated with 93-95% yield and 99.2% purity in HPLC.

EXPERIMENTAL DETAILS

Example 1

Charged 100 gm of sodium dicynamide (1.123 mol) and 153 gm of sodium azide (2.35 mol) along with water (600 ml) at room temperature, into a four neck round bottom flask fitted with mechanical stirrer, condenser, thermometer and one addition funnel. Slowly heated the reaction mixture to 55° C. and at this temperature added 6 molar solution of hydrochloric acid (400 ml) was added into the reaction mixture for a period of 2 to 6 hour. Then reaction mixture was heated to reflux (98° to 100° C.) for 25 hour. After completion of the reaction, cooled the reaction mixture to 55° C. and to it was added 400 ml of 6 molar hydrochloric acid, adjusted the pH to 0.5 (<1). Stirred the reaction mixture at the same temperature for another 1 hour. Then cooled the reaction mixture to 25° to 30° C. or another 1 hour. Filtered the reaction mixture, washed with water (100 ml) to get 158 gm of bis-(1 (2)H-tetrazol-5-yl)-amine monohydrate (yield: 93%) having an HPLC purity of 99% without any further crystallization.

Example 2

Charged 100 gm of sodium dicynamide (1.123 mol) and 153 gm of sodium azide (2.35 mol) along with water (600 ml) at room temperature, into a four neck round bottom flask fitted with mechanical stirrer, condenser, thermometer and one addition funnel. Slowly heated the reaction mixture to 55° C. and at this temperature added the boric acid solution (10 gm in 100 ml of water) for a period of 30 minute. After addition of the boric acid solution, 6 molar solution of hydrochloric acid (400 ml) was added into the reaction mixture for a period of 2 to 6 hour. Then reaction mixture was heated to reflux (98° to 100° C.) for 25 hour. After completion of the reaction, cooled the reaction mixture to 55° C. and to it was added 400 ml of 6 molar hydrochloric acid, adjusted the pH to 0.5 (<1). Stirred the reaction mixture at the same temperature for another 1 hour. Then cooled the reaction mixture to 25° to 30° C. or another 1 hour. Filtered the reaction mixture, washed with water (100 ml) to get 154 gm of wet bis-(1(2) H-tetrazol-5-yl)-amine monohydrate (yield; 90%) having an HPLC purity of 99% without any further crystallization.

We claim:
1. A process for the preparation of Bis-(1(2)H-tetrazol-5-yl)-amine monohydrate of the formula (I), comprising:
   combining sodium dicynamide and sodium azide in water to form a reaction mixture, and
   adding a 6 molar solution of hydrochloric acid in the presence of a catalytic amount of boric acid into the reaction mixture for a period of 2-8 hours at 55° to 58° C.

2. The process for the preparation of Bis-(1(2)H-tetrazol-5-yl)-amine monohydrate of the formula (I) according to claim 1, wherein the reaction achieves a yield of 90% to 93%.

3. The process for the preparation of Bis-(1(2)H-tetrazol-5-yl)-amine monohydrate of the formula (I) according to claim 1, wherein the product is in fine crystalline nature.

4. The process for the preparation of Bis-(1(2)H-tetrazol-5-yl)-amine monohydrate of the formula (I) according to claim 1, further comprising: after adding the hydrochloric acid and boric acid, heating the reaction mixture at reflux temperature.

5. The process for the preparation of Bis-(1(2)H-tetrazol-5-yl)-amine monohydrate of the formula (I) according to claim 4, wherein the reaction mixture is heated at reflux temperature for 25 hours.

6. The process for the preparation of Bis-(1(2)H-tetrazol-5-yl)-amine monohydrate of the formula (I) according to claim 4, further comprising:
   after heating the reaction mixture at reflux temperature, cooling the reaction mixture to 55° C., and
   adjusting the pH of the reaction mixture to less than 1.

7. The process for the preparation of Bis-(1(2)H-tetrazol-5-yl)-amine monohydrate of the formula (I) according to claim 6, further comprising:
   after adjusting the pH to less than 1, cooling the reaction mixture to a temperature of from 25° C. to 30° C., and
   filtering the reaction mixture to obtain the Bis-(1(2)H-tetrazol-5-yl)-amine monohydrate of the formula (I).

* * * * *